(12) United States Patent
Cho et al.

(10) Patent No.: US 11,402,321 B2
(45) Date of Patent: Aug. 2, 2022

(54) HIGH-SENSITIVE BIOSENSOR CHIP USING HIGH EXTINCTION COEFFICIENT MARKER AND DIELECTRIC SUBSTRATE, MEASUREMENT SYSTEM, AND MEASUREMENT METHOD

(71) Applicant: KOREA RESEARCH INSTITUTE OF STANDARD AND SCIENCE, Daejeon (KR)

(72) Inventors: Hyun-mo Cho, Daejeon (KR); Dong-hyung Kim, Seoul (KR); Yong-jai Cho, Daejeon (KR); Won Chegal, Daejeon (KR)

(73) Assignee: KOREA RESEARCH INSTITUTE OF STANDARD AND SCIENCE, Daejeon (KR)

( * ) Notice: Subject to any disclaimer, the term of this patent is extended or adjusted under 35 U.S.C. 154(b) by 85 days.

(21) Appl. No.: 16/982,412

(22) PCT Filed: Aug. 20, 2019

(86) PCT No.: PCT/KR2019/010521
§ 371 (c)(1),
(2) Date: Sep. 18, 2020

(87) PCT Pub. No.: WO2020/040509
PCT Pub. Date: Feb. 27, 2020

(65) Prior Publication Data
US 2021/0072149 A1    Mar. 11, 2021

(30) Foreign Application Priority Data

Aug. 20, 2018 (KR) .......................... 10-2018-0096767

(51) Int. Cl.
*G01N 21/64* (2006.01)
*G01N 21/21* (2006.01)
*G01N 33/52* (2006.01)

(52) U.S. Cl.
CPC .......... *G01N 21/211* (2013.01); *G01N 21/64* (2013.01); *G01N 33/52* (2013.01); *G01N 2021/215* (2013.01)

(58) Field of Classification Search
CPC ...... G01N 21/211; G01N 21/64; G01N 33/52; G01N 2021/215; G01N 33/543; G01N 21/6428; G01N 21/6486
See application file for complete search history.

(56) References Cited

U.S. PATENT DOCUMENTS

| | | | |
|---|---|---|---|
| 6,569,383 B1 | 5/2003 | Nedelkov et al. | |
| 2006/0001872 A1* | 1/2006 | Naya | G01N 21/658 356/301 |

FOREIGN PATENT DOCUMENTS

| | | |
|---|---|---|
| JP | 2005-003561 A | 1/2005 |
| JP | 2011-209097 A | 10/2011 |

(Continued)

*Primary Examiner* — Abdullahi Nur
(74) *Attorney, Agent, or Firm* — Novick, Kim & Lee, PLLC; Jae Youn Kim; Jihun Kim

(57) ABSTRACT

The present chip relates to a high-sensitive biosensor chip using a high extinction coefficient marker and a dielectric substrate, a measurement system, and a measurement method and, more specifically, to an ellipsometry-based high-sensitive biosensor technology or a measurement method using same, the technology amplifying an elliptically polarized signal by a marker having a high extinction coefficient and a dielectric substrate. The marker and the substrate used in the present chip measure a Brewster's angle shift or an elliptical polarization measurement angle with respect to an ultra-low concentration biological material (e.g. antibody or DNA).

11 Claims, 10 Drawing Sheets

(56) References Cited

FOREIGN PATENT DOCUMENTS

| | | |
|---|---|---|
| KR | 10-2009-0064917 A | 6/2009 |
| KR | 10-2017-0075221 A | 7/2017 |
| KR | 10-2018-0062554 A | 6/2018 |

* cited by examiner

| Materials | n (REFRACTIVE INDEX) | k (EXTINCTION COEFFICIENT) |
|---|---|---|
| Beryllium (Be) | 3.3296 | 3.1767 |
| Gold (Au) | 0.4432 | 2.2724 |
| Aluminium (Al) | 0.8842 | 6.4697 |
| Silver (Ag) | 0.1293 | 3.1933 |
| Ruthenium (Ru) | 3.6074 | 4.9509 |
| Titanium (Ti) | 1.8441 | 2.5314 |
| Cobalt (Co) | 1.9965 | 3.735 |
| Iron (Fe) | 2.0351 | 2.8564 |
| Graphite | 2.6687 | 1.5279 |
| Indium (In) | 0.6672 | 4.6505 |
| Osmium (Os) | 4.9211 | 1.838 |

| MARKER TYPE | DIELECTRIC SUBSTRATE SIGNAL (a) | 0.1nm MARKER SIGNAL (b) | SIGNAL AMPLIFICATION DEGREE (b-a) |
|---|---|---|---|
| Be | 6.6986 Ψ | 9.2615 Ψ | 2.5629 Ψ |
| Au | | 7.2417 Ψ | 0.5431 Ψ |
| Al | | 10.202 Ψ | 3.5034 Ψ |
| Ag | | 7.5794 Ψ | 0.8808 Ψ |
| Ru | | 10.606 Ψ | 3.9074 Ψ |
| Ti | | 7.7119 Ψ | 1.0133 Ψ |
| Co | | 8.3874 Ψ | 1.6888 Ψ |
| Fe | | 8.1158 Ψ | 1.4172 Ψ |
| Graphite | | 7.6457 Ψ | 0.9471 Ψ |
| In | | 8.0496 Ψ | 1.351 Ψ |
| Os | | 8.9238 Ψ | 2.2252 Ψ |

FIG. 6

| SUBSTRATE | MARKER | MARKER THICKNESS (nm) | SIGNAL AMPLIFICATION DEGREE ($\Psi$) |
|---|---|---|---|
| Si | $SiO_2$ | 0 | - |
| Si | $SiO_2$ | 1 | 0.2484 $\Psi$ |
| Si | $SiO_2$ | 2 | 0.4969 $\Psi$ |
| Si | $SiO_2$ | 10 | 2.4804 $\Psi$ |

FIG. 10

HIGH-SENSITIVE BIOSENSOR CHIP USING HIGH EXTINCTION COEFFICIENT MARKER AND DIELECTRIC SUBSTRATE, MEASUREMENT SYSTEM, AND MEASUREMENT METHOD

TECHNICAL FIELD

The present invention relates to a highly sensitive biosensor chip, a measurement system, and a measurement method using a marker having a large extinction coefficient and a dielectric substrate, and more specifically, to a technology as an ellipsometry-based highly sensitive biosensor technology that amplifies an elliptical polarization signal by a marker having a large extinction coefficient and a dielectric substrate or a measurement method using the same and to a biosensor technology that measures a shift in Brewster's angle or an elliptical polarization measurement angle with respect to an ultralow-concentration biological substance (for example, an antibody or DNA) by a marker and a substrate used in the present invention.

BACKGROUND ART

Ellipsometry is a measurement technique for measuring a polarization state of reflected light reflected from a surface of a substrate and analyzing a measured value to find a thickness or an optical property of the substrate. The measurement technique is used to evaluate thicknesses and properties of various nanoscale thin films in a nano-thin film manufacturing process of the semiconductor industry. In addition, a constant effort is put into widening an application scope of the measurement technique to the bioindustry so as to apply the measurement technique to interface analysis of a biological substance such as protein, DNA, a virus, or a new drug substance.

In general, an ellipsometer can measure a thickness of a thin film to a nanometer; however, when a thickness is smaller than 0.01 nm, the ellipsometer has a lack of measurement sensitivity required for analysis of a biological substance having a low molecular weight or ultralow concentration and thus a problem arises in that reliability of a measured value is degraded. In order to solve the problem, a light source having a short wavelength is used, and a method for measuring an elliptical polarization signal, which is sensitive to a change in thickness of a substrate, at the Brewster's angle is used. A refractive index does not change depending on a change in thickness of a substrate at the Brewster's angle, and thus the elliptical polarization signal generated by a biological substance can be sensitively measured without an effect of a surrounding environment (for example, temperature). In addition, in order to improve measurement sensitivity by increasing a change in surface thickness of a sensor chip, a large-sized marker can be used to amplify an elliptical polarization signal of a bioreaction.

Surface plasmon resonance (hereinafter, referred to as 'SPR') is a phenomenon in which electrons present on a metal surface are excited by light waves to collectively vibrate in a normal direction of the surface and thereby light energy is absorbed. An SPR sensor using the surface plasmon resonance can perform monitoring in real time and is used in diagnosis of a disease or search for a new drug by signal amplification using a marker. An SPR sensor chip is generally manufactured by coating a glass substrate with a gold thin film having a size of several nanometers. In this case, when a biological substance is connected on a surface of the gold thin film, a resonance angle and reflectivity change to determine connection dynamic characteristics or to perform quantitative analysis. However, a change in refractive index of an inter-layer solution directly affects a shift of a resonance angle, and thus a biological substance having a low molecular weight or ultralow concentration is difficult to measure. In order to correct such a difficulty, expensive additional devices and an advanced analysis algorithm need to be provided.

In an SPR signal amplifying method using a marker, a localized surface plasmon resonance (LSPR) phenomenon is used in some cases. That is a technology of increasing a measurement signal by bonding the marker (for example, gold nanoparticles) and light. However, a signal in response to a bioreaction occurring out of a constant range of a distance (within 200 nm) from a surface of the nano marker is reduced depending on the distance, and thus measurement of a biological substance is limited. In addition, even when metal particles are used as the marker, an effect of an increase in size of the metal particles is a main factor for amplified signal.

As described above, a biosensor (for example, SPR sensor or ellipsometer) which is sensitive to a change in mass of a sensor surface usually uses a size of a marker as a signal amplifying factor. However, the biosensor has a limit in measurement and signal amplification due to a steric hindrance phenomenon in which a size of a marker hinders biological substance bonding reactivity.

A signal amplifying method using an enzyme marker (for example, horseradish peroxidase (HRP)) in the related art can increase a measurement signal of a biological substance in an enzyme reaction with a substrate. However, the substrate needs to be additionally injected in order to cause the enzyme reaction. In addition, a half-life of the reaction is shortened depending on an enzyme storing condition (for example, temperature or period), and thus measurement reproducibility of a biosensor can be degraded.

A fluorescent marker is more stable than an enzyme is, and a large amount of a fluorescent substance can be bonded to a detection substance (for example, detection antibody) to improve a measurement signal. However, a short distance between the fluorescent substances causes a quenching effect of fluorescent energy generated by light, and thus a fluorescent signal is reduced.

When nanoparticles are used as a marker, usually, a measurement signal can be amplified using a size of the marker in surface plasmon resonance (SPR) and a mass sensor such as a quartz crystal microbalance (QCM). However, an increase in size of nanoparticle can cause a steric hindrance phenomenon during a biological bonding reaction, thus, decreasing reaction efficiency.

In addition, in a localized surface plasmon resonance (LSPR) phenomenon which occurs at a surface of a specific nanoparticle (for example, gold nanoparticle), the nanoparticle is bonded to light to increase a measurement signal; however, a bioreaction occurring out of a range of a constant distance from the surface of the nanoparticle causes a reduction in measurement signal depending on the distance, and thus there can be a limit in highly sensitive measurement of a biological substance.

In order to overcome a limit of the signal amplifying method described above, in the present invention, a refractive index of a biological substance bonded to a sensor chip of a dielectric substrate is caused to be significantly changed using a marker having a large extinction coefficient such that an elliptical polarization signal is amplified.

SUMMARY OF INVENTION

Technical Problem

The present invention is proposed to solve the problem in the related art described above, and according to an embodiment of the present invention, an object thereof is to provide an ellipsometric biosensor technology using a marker having a large extinction coefficient and a dielectric substrate, the ellipsometric biosensor technology being as a technology for amplifying a measurement signal of a biosensor with respect to a biological substance and enabling to solve a technical limit of a signal generating method using a known marker (for example, enzyme, fluorescence, or nanoparticle).

According to the embodiment of the present invention, another object thereof is to provide an ellipsometric biosensor technology using a marker having a large extinction coefficient and a dielectric substrate, the ellipsometric biosensor technology enabling to maximize measurement sensitivity by measuring an elliptical polarization signal of a bioreaction at a substrate surface by using the marker having a large extinction coefficient and the dielectric substrate, enabling the shift of the Brewster's angle to be great due to a great change in refractive index when the marker having a large extinction coefficient is attached to the biological substance while a change in elliptical polarization signal is very small with respect to a change in thickness of bio-thin film on the dielectric substrate, and enabling to obtain supersensitive biological substance-connecting characteristics by measuring a shift of the Brewster's angle which is caused by connection of the dielectric substrate to the biological substance to which the marker having a large extinction coefficient is attached or by measuring an elliptical polarization measuring angle.

According to the embodiment of the present invention, still another object thereof is to provide an ellipsometric biosensor technology using a marker having a large extinction coefficient and a dielectric substrate, the ellipsometric biosensor technology enabling to sensitively detect a specific reaction between biological bonding reactions (for example, antigen and antibody) by further amplifying an elliptical polarization signal in biological substance analysis than in known ellipsometry using a size of a marker, and enabling to maximize reaction efficiency by minimizing a steric hindrance phenomenon due to a size of a marker in a biological bonding reaction by measuring a large change in refractive index due to the marker.

According to the embodiment of the present invention, still another object thereof is to provide an ellipsometric biosensor technology using a marker having a large extinction coefficient and a dielectric substrate, the ellipsometric biosensor technology enabling to obtain an amplifying effect as large as dozens of times the effect in a known SPR measurement method, by a large shift of the Brewster's angle due to a change in refractive index of an extinction coefficient rather than a mass of the marker, in measurement of an elliptical polarization signal at the Brewster's angle using the marker having a large extinction coefficient and the dielectric substrate.

According to the embodiment of the present invention, still another object thereof is to provide an ellipsometric biosensor technology using a marker having a large extinction coefficient and a dielectric substrate, the ellipsometric biosensor technology enabling to induce highly sensitive and highly accurate analysis using a mineral property of s sensor substrate and the marker so as to amplify a signal of a biosensor that measures a biological substance, and enabling to maximize a signal amplifying effect in searching a new drug made of a biological substance and or a ultralow molecular weight substance which is present by trace amount as a signal is significantly changed, particularly even by a small difference (<0.1 nm) in the amount of marker having a large extinction coefficient which is bonded to the dielectric substrate.

According to the embodiment of the present invention, still another object thereof is to provide an ellipsometric biosensor technology using a marker having a large extinction coefficient and a dielectric substrate, the ellipsometric biosensor technology enabling to improve analytical performance such as sensitivity, precision, or accuracy as a biosensor that detects an analyte in various fields such as the medical field, the environmental field, and the food field amplifies a measurement signal, enabling to diagnose a disease in an early stage or monitor prognosis after surgery by enhancing the measurement signal of the ellipsometric biosensor to about 50 to 100 times and sensitively detecting a biomarker present at an ultralow concentration in a living body, enabling to accurately monitor a biochemical reaction of a new drug having an ultralow molecular weight so as to minimize an amount of a sample consumed for searching an expensive new drug substance, and enabling to amplify measurement signals of the biosensor by an ellipsometric technique using the dielectric substrate and the marker having a large extinction coefficient, the measurement signal being obtained from various analytes as measurement target substances of the present invention including not only a biological substance such as protein, a cell, and a gene but also a germ and a virus which cause infection through food, a toxic chemical substance, and the like.

On the other hand, technical objects to be achieved by the present invention are not limited to the technical objects mentioned above, and the following description enables other unmentioned technical objects to be clearly understood by a person of ordinary skill in the art to which the present invention belongs.

Solution to Problem

A first object of the present invention may be achieved as a highly sensitive biosensor chip using a marker having a large extinction coefficient and a dielectric substrate, the biosensor chip including: the dielectric substrate to which incident light is incident at a specific incident angle and is reflected from the dielectric substrate; an analyte section which is fixed on the substrate; and the marker that is bonded to the analyte section and amplifies an elliptical polarization signal.

Besides, the marker may have an extinction coefficient which is equal to or larger than a specific value at light having a specific wavelength region.

In addition, the specific value k may be 1.000.

Besides, the analyte section may cause a surface of the dielectric substrate to function as a self-assembled thin film and may fix a capture antibody to the surface, and may include a detection antibody which is attached to the marker and a biological bonding substance which is bonded between the detection antibody and the capture antibody and becomes an analysis target.

In addition, the biological bonding substance may be protein, DNA, RNA, a cell, a peptide, or a bacterium.

A second object of the present invention may be achieved as a highly sensitive measurement system using a marker having a large extinction coefficient and a dielectric substrate, the measurement system including: a polarization generating unit that generates polarized light; the biosensor chip according to the first object mentioned above to which the polarized light generated at the polarization generating unit is incident at a specific incident angle; and a polarization detecting unit that measures a polarization signal from reflected light reflected from the biosensor chip.

Besides, the incident angle may be Brewster's angle with respect to the dielectric substrate.

In addition, the incident angle may be a maximum difference between a psi value of the dielectric substrate and a psi value of the marker.

Besides, the polarization generating unit may include a light source and a polarizer.

In addition, the polarization detecting unit may include an analyzer, a photodetector, and a calculation processor.

A third object of the present invention may be achieved as a highly sensitive measurement method using a marker having a large extinction coefficient and a dielectric substrate, the measurement method using the highly sensitive measurement system using a marker having a large extinction coefficient and a dielectric substrate according to the second object mentioned above, the measurement method including: a step of generating polarized light at a polarization generating unit; a step of causing the polarized light generated at the polarization generating unit to be incident to the biosensor chip at a specific incident angle; a step of amplifying a signal by the marker fixed to an analyte attached to the dielectric substrate; and a step of measuring a polarization signal from reflected light incident to the polarization detecting unit, after the reflected light is reflected from the biosensor chip.

Besides, the marker may have an extinction coefficient k which is equal to or larger than 1.000 at light having a specific wavelength region.

In addition, a surface of the dielectric substrate may be caused to function as a self-assembled thin film to fix a capture antibody to the surface, and a detection antibody which is attached to the marker and a biological bonding substance which is bonded between the detection antibody and the capture antibody and becomes an analysis target may be provided.

Advantageous Effects of Invention

According to an ellipsometric biosensor technology using a marker having a large extinction coefficient and a dielectric substrate according to an embodiment of the present invention, as a technology for amplifying a measurement signal of the ellipsometric biosensor with respect to a biological substance, the ellipsometric biosensor technology has an effect of solving a technical limit of a signal generating method using a known marker (for example, enzyme, fluorescence, or nanoparticle).

According to the ellipsometric biosensor technology using a marker having a large extinction coefficient and a dielectric substrate according to the embodiment of the present invention, the ellipsometric biosensor technology has effects of maximizing measurement sensitivity by measuring an elliptical polarization signal of a bioreaction at a substrate surface by using the marker having a large extinction coefficient and the dielectric substrate, making the shift of the Brewster's angle to be great due to a great change in refractive index when the marker having a large extinction coefficient is attached to the biological substance while a change in elliptical polarization signal is very small with respect to a change in thickness of bio-thin film on the dielectric substrate, and obtaining supersensitive biological substance-connecting characteristics by measuring a shift of the Brewster's angle which is caused by connection of the dielectric substrate to the biological substance to which the marker having a large extinction coefficient is attached or by measuring an elliptical polarization measuring angle.

According to the ellipsometric biosensor technology using a marker having a large extinction coefficient and a dielectric substrate according to the embodiment of the present invention, the ellipsometric biosensor technology has effects of sensitively detecting a specific reaction between biological bonding reactions (for example, antigen and antibody) by further amplifying an elliptical polarization signal in biological substance analysis than in known ellipsometry using a size of a marker, and maximizing reaction efficiency by minimizing a steric hindrance phenomenon due to a size of a marker in a biological bonding reaction by measuring a large change in refractive index due to the marker.

According to the ellipsometric biosensor technology using a marker having a large extinction coefficient and a dielectric substrate according to the embodiment of the present invention, the ellipsometric biosensor technology has an effect of obtaining an amplifying effect as large as dozens of times the effect in a known SPR measurement method, by a large shift of the Brewster's angle due to a change in refractive index of an extinction coefficient rather than a mass of the marker, in measurement of an elliptical polarization signal at the Brewster's angle using the marker having a large extinction coefficient and the dielectric substrate.

According to the ellipsometric biosensor technology using a marker having a large extinction coefficient and a dielectric substrate according to the embodiment of the present invention, the ellipsometric biosensor technology has an effect of inducing highly sensitive and highly accurate analysis using a mineral property of s sensor substrate and the marker so as to amplify a signal of a biosensor that measures a biological substance, and maximizing a signal amplifying effect in searching a new drug made of a biological substance and or a ultralow molecular weight substance which is present by trace amount as a signal is significantly changed, particularly even by a small difference (<0.1 nm) in the amount of marker having a large extinction coefficient which is bonded to the dielectric substrate.

According to the ellipsometric biosensor technology using a marker having a large extinction coefficient and a dielectric substrate according to the embodiment of the present invention, the ellipsometric biosensor technology has effects of improving analytical performance such as sensitivity, precision, or accuracy as a biosensor that detects an analyte in various fields such as the medical field, the environmental field, and the food field amplifies a measurement signal, diagnosing a disease in an early stage or monitor prognosis after surgery by enhancing the measurement signal of the ellipsometric biosensor to about 50 to 100 times and sensitively detecting a biomarker present at an ultralow concentration in a living body, accurately monitoring a biochemical reaction of a new drug having an ultralow molecular weight so as to minimize an amount of a sample consumed for searching an expensive new drug substance, and amplifying measurement signals of the biosensor by an ellipsometric technique using the dielectric substrate and the marker having a large extinction coefficient, the measurement signal being obtained from various analytes as measurement target substances of the present invention including not only a biological substance such as protein, a cell, and a gene but also a germ and a virus which cause infection through food, a toxic chemical substance, and the like.

On the other hand, technical objects to be achieved by the present invention are not limited to the technical objects mentioned above, and the following description enables other unmentioned technical objects to be clearly understood by a person of ordinary skill in the art to which the present invention belongs.

BRIEF DESCRIPTION OF DRAWINGS

The following drawings accompanied in this specification illustrate a preferred embodiment of the present invention and are provided to cause the technical idea of the present invention to be better understood with the detailed description of the invention, and thus the present invention is not to be understood by being limited only to illustration of the drawings.

FIGS. 4 and 5 are a refractive index and extinction coefficient table of a candidate substance classified in accordance with a criterion for selecting a marker having a large extinction coefficient according to the embodiment of the present invention.

FIG. 6 is a graph illustrating amplification of an elliptical polarization signal when a dielectric substrate and an Ru marker are applied.

FIGS. 9 and 10 illustrate comparison of elliptical polarization signals depending on a thickness of a marker (for example, $SiO_2$) having a small extinction coefficient in a specific wavelength region in order to check a signal amplification effect according to the embodiment of the present invention.

DESCRIPTION OF EMBODIMENTS

Figure 1:
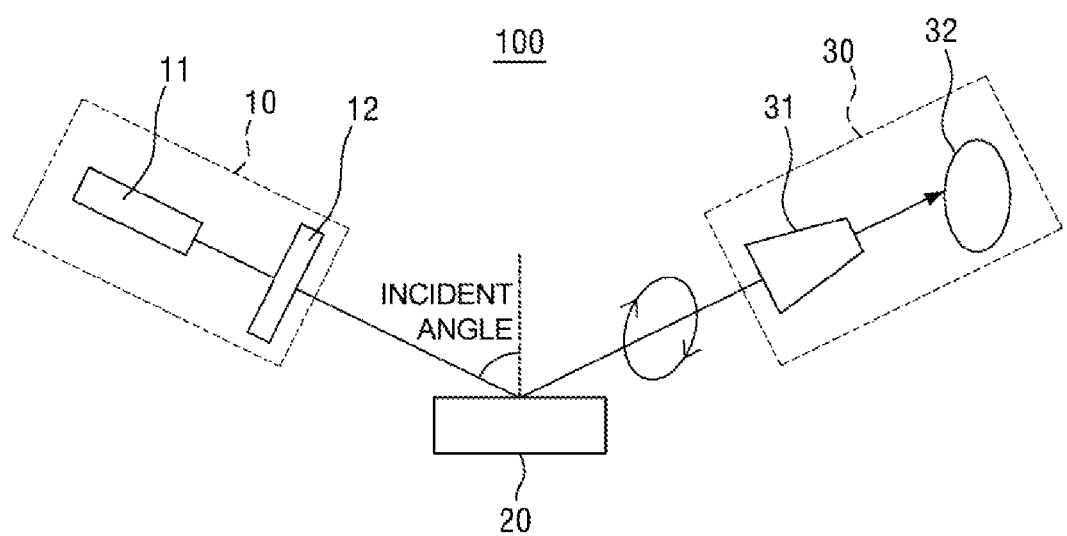
FIG. 1 is a configurational diagram of a measurement system using a biosensor according to an embodiment of the present invention.

The objects, other objects, characteristics, and advantages of the present invention described above are to be easily understood through the following preferred embodiments related to the accompanying drawings. However, the present invention is not limited to the embodiments described here and can be realized as other embodiments. Instead, the embodiments introduced here are provided to make the disclosed details thorough and complete and to allow ideas of the present invention to be sufficiently understood by those skilled in the art.

In this specification, a case where a certain configurational element is described to be present on another configurational element means a case where the configurational element can be directly formed on the other configurational element or a third configurational element can be interposed between the configurational elements. In addition, in the drawings, configurational elements are illustrated to have an enlarged thickness for effective description of the technical details.

The embodiments described in this specification are to be described with reference to cross-sectional views and/or plan views which are ideally illustrated views of the present invention. In the drawings, films and regions are illustrated to have an enlarged thickness for effective description of the technical details. Consequently, a shape in an illustrated view can be changed due to a manufacturing technology, a tolerance, and/or the like. Consequently, the embodiments of the present invention are not limited to specific shapes illustrated in the drawings but include a change in shape which occurs according to a manufacturing process. For example, a region illustrated to have a right angle can have a shape which is rounded or has predetermined curvature. Consequently, regions illustrated in the drawings have a property, and shapes of the regions illustrated in the drawings are provided to illustrate specific shapes of regions of an element and are not provided to limit a scope of the invention. In various embodiments in this specification, terms of first, second, and the like are used to describe various configurational elements; however, the configurational elements are not to be limited by these terms. These terms are used only to distinguish a certain configurational element from another configurational element. The embodiments described and illustrated here also include complementary embodiments thereof.

Terms used in this specification are used to describe embodiments and are not used to limit the present invention. In this specification, a singular form includes meaning of a plural form unless otherwise described particularly in the description. When terms such as 'comprises' and/or 'comprising' is used in the specification, a mentioned configurational element does not exclude presence or addition of one or more other configurational elements.

In the description of the following specific embodiments, several specific details are provided to more specifically describe the invention and to gain a better understanding of the invention. However, a reader who has knowledge in the art to understand the present invention can recognize that the present invention can be used without these several specific details. The following is mentioned in advance. In some cases, parts which are commonly known but are not closely related to the invention in a description of invention are not described in order to prevent confusion from being caused for no good reason in the description of the present invention.

Hereinafter, a highly sensitive measurement system 100 using a marker having a large extinction coefficient and a dielectric substrate according to an embodiment of the present invention is basically configured to include a highly sensitive biosensor chip 20 using a marker having a large extinction coefficient and a dielectric substrate.

First, FIG. 1 illustrates a configurational diagram of the measurement system 100 using the biosensor chip 20 according to an embodiment of the present invention. As illustrated in FIG. 1, the measurement system 100 according to the embodiment of the present invention is configured to include a polarization generating unit 10 that generates polarized light; the biosensor chip 20 to which the polarized light generated at the polarization generating unit 10 is incident at a specific incident angle and which amplifies an elliptical polarization signal; and a polarization detecting unit 30 that measures the elliptical polarization signal from reflected light reflected from the biosensor chip 20. In other words, in the embodiment of the present invention, a technology for amplifying a signal by an ellipsometric biosensor using a dielectric substrate 21 and a marker having a large extinction coefficient is described. In order to realize the embodiment, a short wavelength ellipsometer configured to include a light source 11, a polarizer 12, a sample piece, an analyzer 31, and a measuring instrument is used.

The polarization generating unit 10 according to the embodiment of the present invention generates polarized light and can have the light source 11 and the polarizer 12.

Examples of the light source 11 can include various types of lamps which emit monochromatic light or white light having infrared, visible light, or ultraviolet wavelength ranges, a semiconductor laser diode (LD) including a light-emitting diode (LED), a solid-, liquid-, or gas-state laser, and a laser diode, and the like. In addition, the light source 11 can have a structure which can vary a wavelength depending on a structure of an optical system. Besides, the polarizer 12 can be configured to be rotatable, or another polarization modulating means can be further provided.

Besides, the polarization detecting unit 30 is to measure an elliptical polarization signal from the reflected light reflected from the biosensor chip 20. In other words, the polarization detecting unit receives the reflected light and detects a polarization change thereof. The polarization detecting unit 30 includes the analyzer 31 and a measurement unit 32, and the measurement unit 32 can include a detector, a calculation processor, and the like. In addition, a compensator and a spectroscope can be provided.

The analyzer 31 corresponds to the polarizer 12 and have a polarizing plate to re-polarize reflected light, thereby, being capable of controlling a degree of polarization of the reflected light or a direction of a polarization plane. The analyzer 31 can be configured to be rotatable according to a structure of an optical system, or another polarization modulating means that can perform a function of a phase change or removal of a polarization component can be further provided.

The detector fulfills a function of detecting polarized reflected light to obtain optical data and converting the optical data into an electrical signal. In this case, the optical data contains information about a change in polarization state of the reflected light. An example of the detector can include a CCD-type solid imaging element, a photomultiplier tube (PMT), or a silicon photodiode.

The calculation processor acquires an electrical signal from the detector and derives a measured value. The calculation processor has a predetermined analysis program using a reflectivity measuring method and ellipsometry which is installed to cause the calculation processor to extract and analyze the optical data converted into the electrical signal, thereby deriving a measured value such as an adsorption concentration of a sample, a thickness of an adsorption layer, an adsorption constant, a dissociation constant, or a refractive index. In this case, it is preferable that the calculation processor derives the measured value by obtaining ellipsometric constants $\Psi$ and $\Delta$ related to a phase difference of the ellipsometry in order to improve measurement sensitivity.

Figure 2:
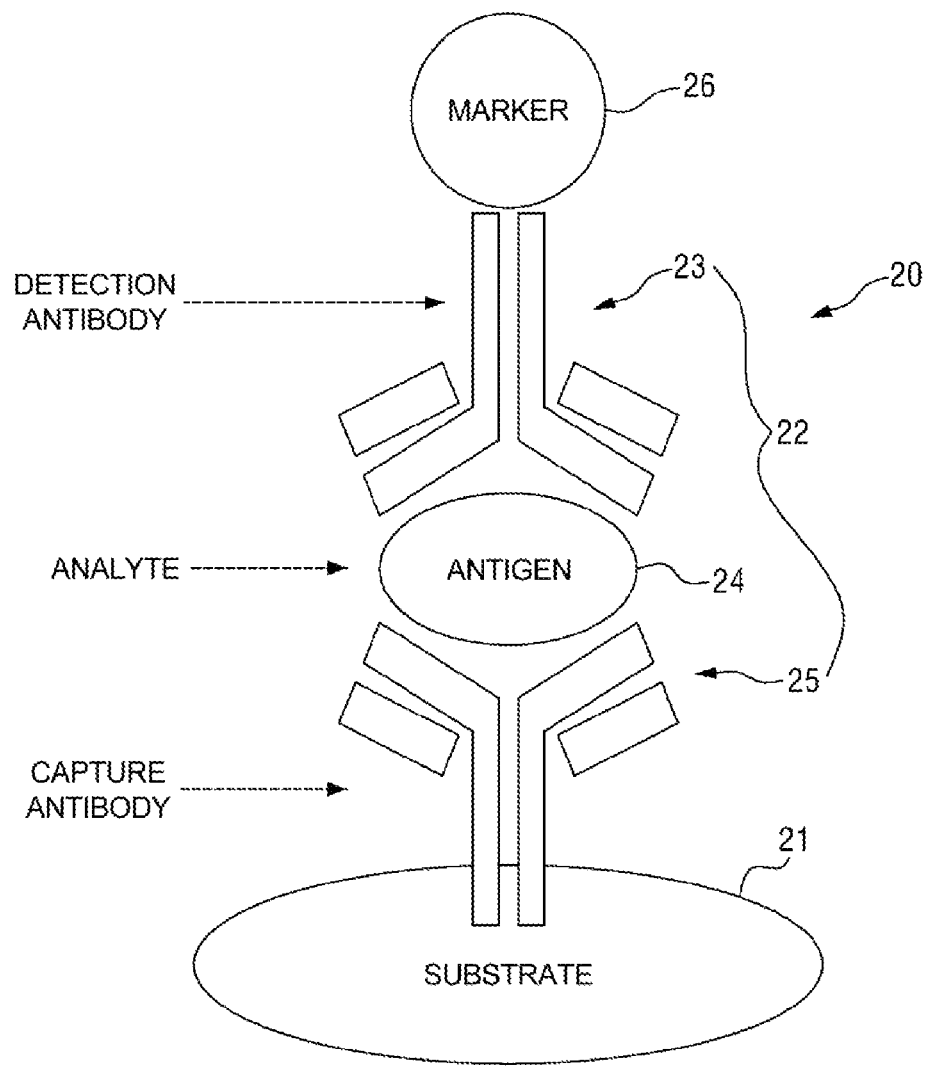
FIG. 2 is a schematic diagram of a highly sensitive biosensor chip using a marker having a large extinction coefficient and a dielectric substrate according to the embodiment of the present invention.
Figure 3:
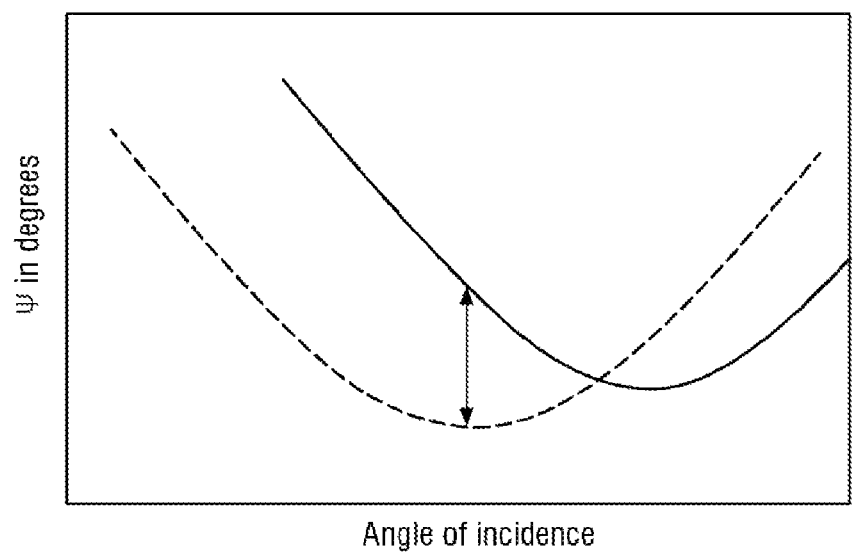
FIG. 3 is a graph illustrating amplification of an elliptical polarization signal by the marker according to the embodiment of the present invention.

FIG. 2 is a schematic diagram of the highly sensitive biosensor chip 20 using a marker having a large extinction coefficient and a dielectric substrate according to the embodiment of the present invention. In addition, FIG. 3 is a graph illustrating amplification of an elliptical polarization signal by a marker 26 according to the embodiment of the present invention. In other words, FIG. 2 is a diagram illustrating a technical concept of amplification of the elliptical polarization signal. The drawing indicates that the dielectric substrate 21 and the marker 26 having a large extinction coefficient are used to amplify the elliptical polarization signal of the ellipsometric biosensor chip 20.

The biosensor chip 20 according to the embodiment of the present invention uses the dielectric substrate 21, and the biosensor chip 20 is manufactured by fixing a biological bonding substance (for example, capture antibody or genome) to a surface of the dielectric substrate. An analyte in a biological sample is reacted and bonded with the biological bonding substance fixed to a sensor surface, and the marker 26 having a large extinction coefficient is attached to a detection substance 23 (for example, detection antibody or genome) and generates a high elliptical polarization signal with respect to the analyte.

In this case, as the marker 26, a marker 26 (k>1.000) having a large extinction coefficient at light having a specific wavelength region is used. In addition, an angle at which a laser beam is incident to the dielectric substrate 21 can be determined by basically applying the Brewster's angle with respect to the dielectric substrate 21 and also can be set to a specific incident angle at which a difference between a psi value of the dielectric substrate 21 and a psi value of the marker 26 is the largest.

As illustrated in FIG. 2, the highly sensitive biosensor chip 20 using the marker 26 having a large extinction coefficient and the dielectric substrate 21 according to the embodiment of the present invention is configured to include the dielectric substrate 21 to which incident light is incident at a specific incident angle and is reflected from the dielectric substrate; an analyte section 22 which is fixed on the substrate 21; and the marker 26 having a large extinction coefficient which is bonded to the analyte section 22 and amplifies an elliptical polarization signal.

The analyte section 22 according to the embodiment causes a surface of the dielectric substrate 21 to function as a self-assembled thin film and fixes a capture antibody 25 to the surface, and includes a detection antibody 23 which is attached to the marker 26 and a biological bonding substance 24 which is bonded between the detection antibody 23 and the capture antibody 25 and becomes an analysis target. Examples of the biological bonding substance 24 can include protein, DNA, RNA, a cell, a peptide, a bacterium, and the like.

In other words, as illustrated in FIG. 2, the surface of the dielectric substrate 21 is caused to function as a self-assembled thin film, and fix the capture antibody 25. The detection antibody 23 can be attached to the marker 26 having a large extinction coefficient, and the marker can induce a sandwich bonding reaction with the target substance. In this case, the marker 26 having a large extinction coefficient which is formed at the dielectric substrate 21 amplifies the elliptical polarization signal (psi, $\Psi$) by causing a large change in refractive index based on the specific incident angle (for example, Brewster's angle).

Besides, the marker 26 has an extinction coefficient which is equal to or larger than a specific value at light having a specific wavelength region. In the embodiment of the present invention, the specific value k corresponds to 1.000.

Figure 5:
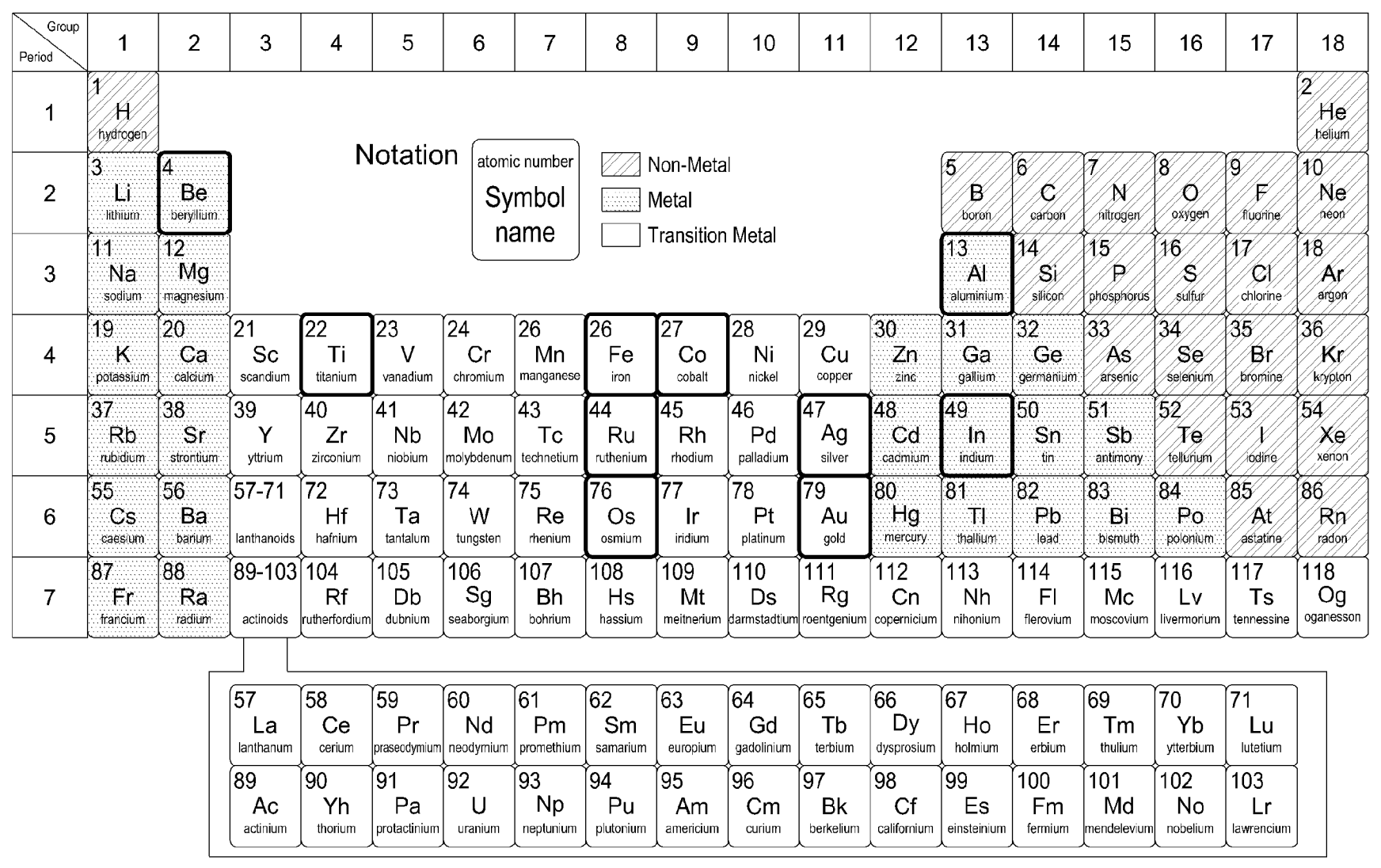

FIGS. 4 and 5 are a refractive index and extinction coefficient table of a candidate substance classified in accordance with a criterion for selecting the marker 26 having a large extinction coefficient according to the embodiment of the present invention.

In other words, FIGS. 4 and 5 provide the criterion for selecting the marker 26 having a large extinction coefficient k. In the embodiment of the present invention, a mineral property of the marker 26 with respect to a specific wavelength (532 nm) is classified as a complex refractive index containing the refractive index and the extinction coefficient. The marker 26 is selected particularly based on the extinction coefficient k larger than 1.000. Individual candidate substances of the marker have a different extinction coefficient depending on a wavelength of the light source 11; however, the criterion of the extinction coefficient for selecting the marker 26 is the same even at a light source 11 having a different wavelength.

Figure 7:
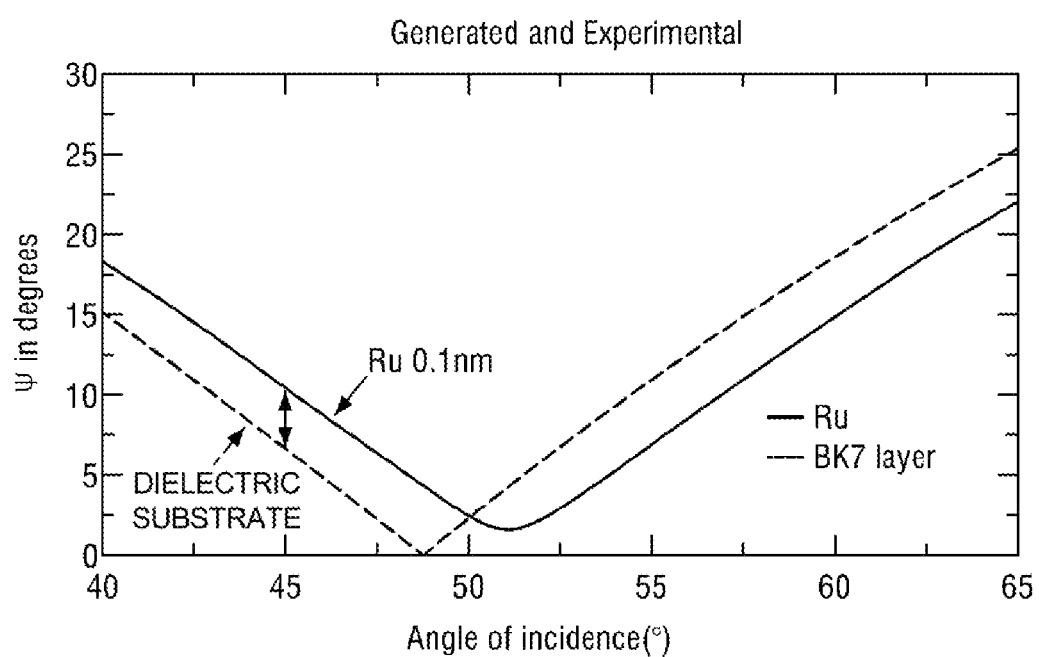
FIG. 7 illustrates graphs indicating a dielectric substrate signal, and a marker signal depending on a marker according to the embodiment of the present invention, a signal amplification degree.
Figure 8:
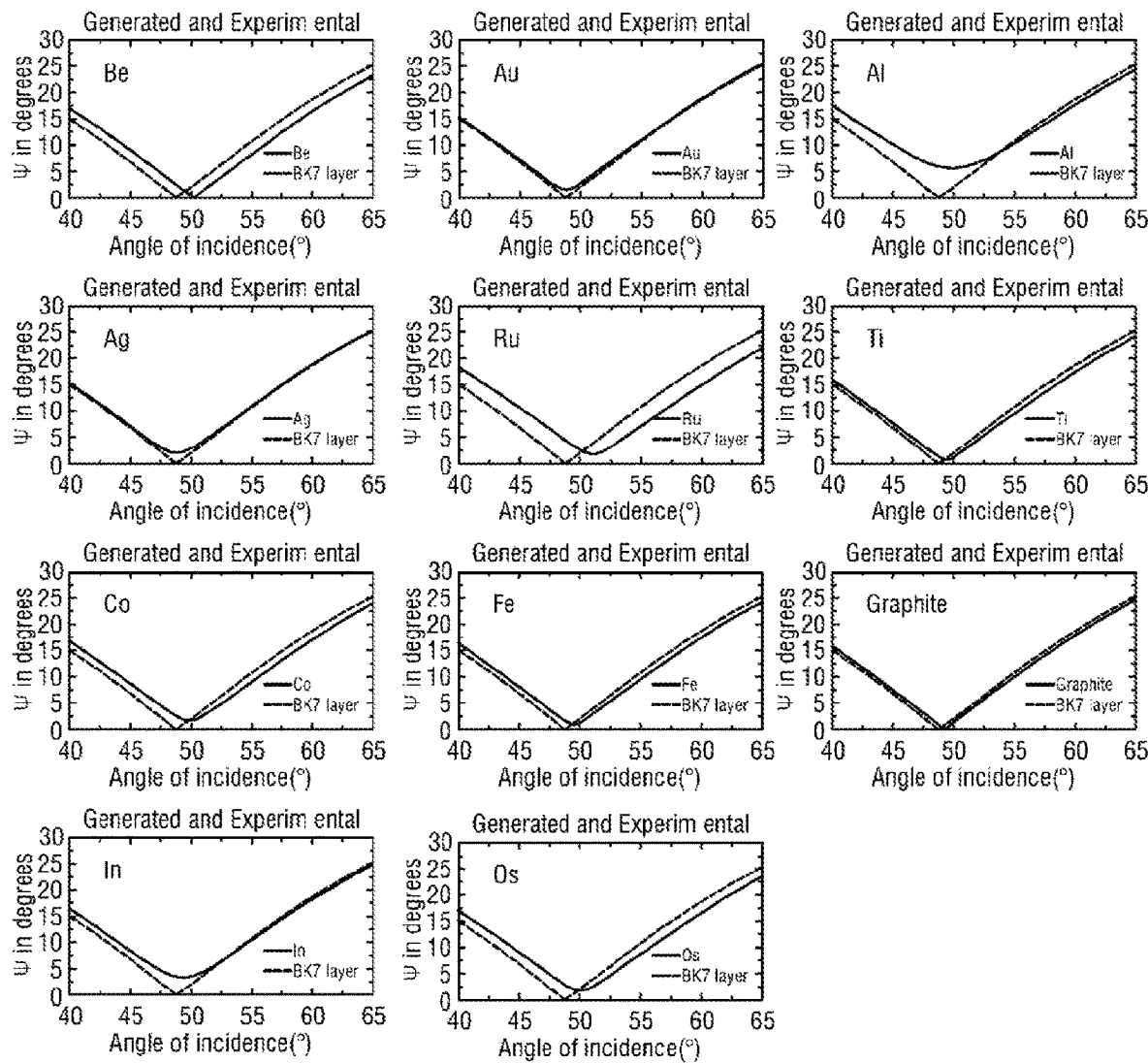
FIG. 8 is a graph illustrating amplification of an elliptical polarization signal depending on the marker according to the embodiment of the present invention.

FIG. 6 is a graph illustrating amplification of the elliptical polarization signal when the dielectric substrate 21 and an Ru marker 26 are applied. FIG. 7 illustrates graphs indicating a dielectric substrate signal, a marker (26) signal depending on the marker 26 according to the embodiment of the present invention, and a signal amplification degree. In addition, FIG. 8 is a graph illustrating amplification of an elliptical polarization signal depending on the marker 26 according to the embodiment of the present invention.

In other words, FIG. 6 illustrates a psi value of a signal amplification degree estimated at a specific incident angle (for example, incident angle of 45°) when the marker 26 having a large extinction coefficient is bonded by 0.1 nm at the dielectric substrate 21. According to the embodiment of the present invention, signal amplification due to a size of the marker 26 is not used, but a mineral property of the marker 26 having a large extinction coefficient which causes a large change in refractive index with the dielectric substrate 21 is used, and thus the elliptical polarization signal is largely amplified even with a size having a nanometer or smaller. That enables a signal to be amplified 100 times than a signal from the silicon marker 26 of 0.1 nm having a silicon oxide film.

Figure 9:
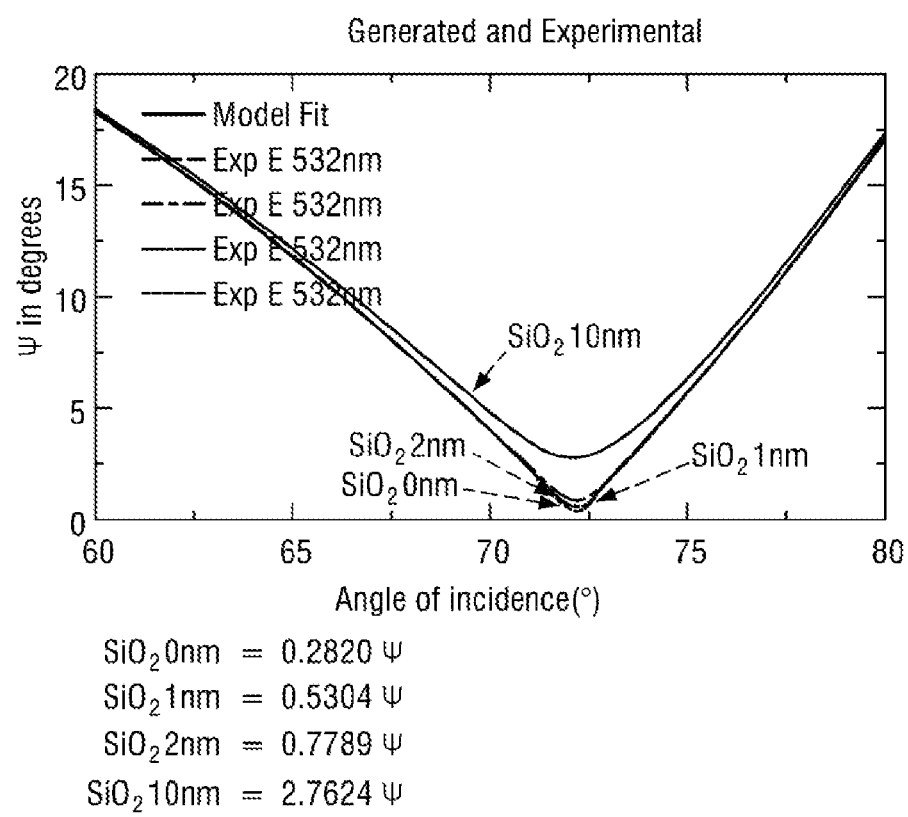

FIGS. 9 and 10 illustrate comparison of elliptical polarization signals depending on a thickness of a marker (for example, $SiO_2$) having a small extinction coefficient at a specific wavelength region in order to check a signal amplification effect according to the embodiment of the present invention. As a result, the following is confirmed. As illustrated in FIGS. 9 and 10, when a marker having a low extinction coefficient is bonded by 2 nm or larger to the sensor surface, the elliptical polarization signal is increased to 0.5000 psi or larger. That can be an indication of obtaining an elliptical polarization signal lower than 100 times the signal by the marker 26 having a large extinction coefficient provided in the embodiment of the present invention.

In addition, the device and method described above can have a configuration in which all or a part of individual embodiments are selectively combined such that the configurations and methods of the embodiments described above are not to be limitedly applied, but the above-described embodiments can be variously modified.

What is claimed is:

1. A biosensor chip using a marker having a extinction coefficient, the biosensor chip comprising:
   a dielectric substrate to which incident light is emitted incident at a specific incident angle such that the incident light is reflected from the dielectric substrate; and
   an analyte section which is fixed on the dielectric substrate,
   wherein the marker is bonded to the analyte section and configured to amplify an elliptical polarization signal,
   wherein a surface of the dielectric substrate functions as a self-assembled thin film and fixes a capture antibody to the surface, and
   wherein the analyte section includes the capture antibody, a detection antibody attached to the marker, and a biological bonding substance which is bonded between the detection antibody and the capture antibody and becomes an analysis target.

2. The biosensor chip according to claim 1, wherein the extinction coefficient of the marker is equal to or greater than a specific value k at light having a specific wavelength region.

3. The biosensor chip according to claim 2, wherein the specific value k is 1.000.

4. A measurement system comprising:
   a polarization generating unit that is configured to generate polarized light;
   the biosensor chip according to claim 1 to which the polarized light generated at the polarization generating unit is emitted incident at a specific incident angle; and
   a polarization detecting unit that is configured to measure a polarization signal from light reflected from the biosensor chip.

5. The measurement system according to claim 4, wherein the specific incident angle is Brewster's angle with respect to the dielectric substrate.

6. The measurement system according to claim 4, wherein the specific incident angle is a maximum difference between a psi value of the dielectric substrate and a psi value of the marker.

7. The measurement system according to claim 4, wherein the polarization generating unit includes a light source and a polarizer.

8. The measurement system according to claim 4, wherein the polarization detecting unit includes an analyzer, a photodetector, and a calculation processor.

9. A measurement method using the measurement system according to claim 4, the measurement method comprising:
   generating polarized light at the polarization generating unit;
   emitting the polarized light generated at the polarization generating unit to be incident to the biosensor chip at a specific incident angle;
   amplifying a signal by the marker fixed to the analyte attached to the dielectric substrate; and
   measuring a polarization signal from reflected light incident to the polarization detecting unit, after the reflected light is reflected from the biosensor chip.

10. The measurement method according to claim 9, wherein the marker has an extinction coefficient k which is equal to or greater than 1.000 with light having a specific wavelength region.

11. The measurement method according to claim 10, wherein the surface of the dielectric substrate is caused to function as a self-assembled thin film to fix a capture antibody to the surface, and a detection antibody which is attached to the marker and a biological bonding substance which is bonded between the detection antibody and the capture antibody and becomes an analysis target are provided.

* * * * *